(12) United States Patent
Kwak (10) Patent No.: US 8,631,254 B2
(45) Date of Patent: Jan. 14, 2014

(54) SECURE WAKE-UP METHOD, WAKE-UP AUTHENTICATION CODE GENERATION AND UPDATING METHOD OF A NETWORK DEVICE AND A NETWORK CONTROL DEVICE IN A WIRELESS BODY AREA NETWORK

(75) Inventor: Kyungsup Kwak, Incheon (KR)

(73) Assignee: Inha-Industry Partnership Institute, Incheon (KR)

( * ) Notice: Subject to any disclaimer, the term of this patent is extended or adjusted under 35 U.S.C. 154(b) by 439 days.

(21) Appl. No.: 12/892,923

(22) Filed: Sep. 29, 2010

(65) Prior Publication Data

US 2011/0107075 A1    May 5, 2011

(30) Foreign Application Priority Data

Oct. 29, 2009    (KR) .................. 10-2009-0103489

(51) Int. Cl.
*G06F 1/00*    (2006.01)
*G08B 23/00*    (2006.01)
*G06F 9/00*    (2006.01)

(52) U.S. Cl.
USPC ........................... 713/300; 340/573.1; 713/2

(58) Field of Classification Search
USPC ................................ 713/2, 300; 340/573.1
See application file for complete search history.

(56) References Cited

U.S. PATENT DOCUMENTS

| 2003/0104848 A1* | 6/2003 | Brideglall | 455/574 |
| 2004/0027244 A9* | 2/2004 | Menard | 340/573.1 |
| 2008/0122625 A1 | 5/2008 | Jung et al. | |
| 2009/0023391 A1* | 1/2009 | Falck | 455/41.2 |
| 2009/0082635 A1* | 3/2009 | Baldus et al. | 600/300 |
| 2009/0282249 A1* | 11/2009 | Aamknecht et al. | 713/171 |

FOREIGN PATENT DOCUMENTS

| KR | 2006-0022975 A | 3/2006 |
| WO | 2009078575 A1 | 6/2009 |

OTHER PUBLICATIONS

Project: IEEE P802.15 Working Group for Wireless Personal Area Networks (WPANs); doc.: IEEE 802.15-09-0366-00-0006; May 2009.
Office Action in Corresponding Chinese Application 201010245230.6.

* cited by examiner

*Primary Examiner* — Thomas Lee
*Assistant Examiner* — Terrell Johnson
(74) *Attorney, Agent, or Firm* — Saliwanchik, Lloyd & Eisenschenk (57) ABSTRACT

A network device and a network control device in a Wireless Body Area Network (WBAN), and a secure wake-up method and a wake-up authentication code (WAC) generation method of the network device and the network control device are provided. The network device includes a wake-up circuit to receive a wake-up radio signal from a network control device using a Radio-Frequency Identification (RFID) receiver, to compare a WAC contained in the received wake-up radio signal with a WAC stored in advance, and to determine whether to wake up a main circuit unit, the network control device being contained in the WBAN; and the main circuit unit to be woken up in response to an interrupt signal from the wake-up circuit.

4 Claims, 9 Drawing Sheets

| 8 | 32 | 16 | bits |
|---|---|---|---|
| Start Package | Wake-up Authentication Code (WAC) | CRC | |
| MHR | Frame Body | MFR | |

SECURE WAKE-UP METHOD, WAKE-UP AUTHENTICATION CODE GENERATION AND UPDATING METHOD OF A NETWORK DEVICE AND A NETWORK CONTROL DEVICE IN A WIRELESS BODY AREA NETWORK

CROSS-REFERENCE TO RELATED APPLICATION

This application claims the benefit of Korean Patent Application No. 10-2009-0103489, filed on Oct. 29, 2009, in the Korean Intellectual Property Office, the disclosure of which is incorporated herein by reference.

BACKGROUND

1. Field of the Invention

The present invention relates to a network device and a network control device in a Wireless Body Area Network (WBAN), and a secure wake-up method and a wake-up authentication code (WAC) generation method of the network device and the network control device.

2. Description of the Related Art

Wireless Body Area Networks (WBANs) act to wirelessly sense and monitor a person's vital functions, and are based on a low cost Wireless Sensor Network (WSN) technology. WBANs may greatly benefit personal health-care in hospitals, residences and work environments, and may provide a better quality of life. One bottleneck in WBANs is that it is very difficult or inconvenient to recharge batteries of Body Area Network nodes (BNs). To increase the lifespan of devices in a WSN, various wake-up schemes have been proposed. However, most of these schemes are not designed specifically for a WBAN having a star topology, and none take security into consideration in a wake-up procedure.

Schemes to protect a wake-up radio signal are still under research. Particularly, security has become a major issue in a WBAN using a wake-up radio signal. Serious consequences can result when an external user may arbitrarily wake up BNs which are implanted and in sleep state, regardless of whether the external user wakes up the BNs unintentionally or maliciously.

Accordingly, there is a desire for a new secure wake-up scheme and method.

SUMMARY

An aspect of example embodiments provides a network device that may wake up a main circuit unit using an energy obtained from a wake-up radio signal, which is received using a Radio-Frequency Identification (RFID) receiver in an Industrial, Scientific and Medical (ISM) band, may authenticate the wake-up radio signal based on a Wake-up Authentication Code (WAC) contained in the wake-up radio signal, and may communicate with a network control device in a Medical Implant Communication Service (MICS) frequency band, and provides a secure wake-up method of the network device.

Another aspect of example embodiments provides a network control device that may transmit a wake-up radio signal to a network device using an RFID receiver, may receive a response signal from the network device which is woken up in response to the wake-up radio signal, and may communicate with the network device, and provides a secure wake-up method of the network control device.

Still another aspect of example embodiments provides a method of generating a WAC using at least one of a counter, which is obtained based on the number of times a network device is woken up, an address for the network device, an address for a network control device, and a key shared between the network device and the network control device.

According to an aspect of example embodiments, there is provided a network device contained in a Wireless Body Area Network (WBAN), the network device including a wake-up circuit to receive a wake-up radio signal from a network control device using an RFID receiver, to compare a WAC contained in the received wake-up radio signal with a WAC stored in advance, and to determine whether to wake up a main circuit unit, the network control device being contained in the WBAN; and the main circuit unit to be woken up in response to an interrupt signal from the wake-up circuit.

The interrupt signal may be generated by the wake-up circuit using an energy contained in the wake-up radio signal.

The main circuit unit may include a communication circuit to transmit a response signal to the network control device after the main circuit unit is woken up in response to the interrupt signal, and a security circuit to update a counter and to update the stored WAC based on at least one of the updated counter, an address for the security circuit, an address for the network control device, and a key shared with the network control device.

After the security circuit updates the WAC, the communication circuit may transmit data to the network control device, the data being sensed or monitored.

According to another aspect of example embodiments, there is provided a network control device contained in a WBAN, the network control device including a wake-up radio signal transmitter to transmit a wake-up radio signal containing a WAC to a network device using an RFID receiver, the network device being contained in the WBAN; and a response signal receiver to receive a response signal from the network device when a main circuit unit of the network device is woken up based on the WAC. In this instance, an interrupt signal may be generated using an energy contained in the wake-up radio signal, to wake up the main circuit.

According to another aspect of example embodiments, there is provided a secure wake-up method in a network device contained in a WBAN, the secure wake-up method including receiving, by a wake-up circuit of the network device, a wake-up radio signal from a network control device using an RFID receiver, the network control device being contained in the WBAN; comparing, by the wake-up circuit, a WAC contained in the received wake-up radio signal with a WAC stored in advance, and determining whether to wake up a main circuit unit of the network device; generating, by the wake-up circuit, an interrupt signal using an energy contained in the wake-up radio signal, and transmitting the generated interrupt signal to the main circuit unit; transmitting, by a communication circuit of the main circuit unit, a response signal to the network control device, the main circuit unit being woken up in response to the interrupt signal; updating, by a security circuit of the main circuit unit, a counter, and updating the stored WAC based on at least one of the updated counter, an address for the security circuit, an address for the network control device, and a key shared with the network control device; and transmitting, by the communication circuit, data to the network control device, the data being sensed or monitored.

According to another aspect of example embodiments, there is provided a secure wake-up method in a network control device contained in a WBAN, the secure wake-up method including transmitting, by a wake-up radio signal transmitter of the network control device, a wake-up radio signal containing a WAC to a network device using an RFID receiver, the network device being contained in the WBAN; receiving, by a response signal receiver of the network control device, a response signal from the network device when a main circuit unit of the network device is woken up based on the WAC; updating, by a security circuit of the network control device, a counter, and updating the WAC based on at least one of the updated counter, an address for the security circuit, an address for the network device, and a key shared with the network device; and receiving, by a data receiver of the network control device, data from the network device, the data being sensed or monitored. In this instance, to wake up the main circuit unit of the network device, an interrupt signal may be generated using an energy contained in the wake-up radio signal.

According to another aspect of example embodiments, there is provided a method of generating a WAC in a network control device or in a network device, the method including generating an initial input value based on at least one of a counter, an address for the network control device and an address for the network device; performing a bitwise operation on the initial input value and an initial vector, to generate an input value; and generating a WAC using the input value, the AES algorithm and a key shared between the network control device and the network device. In this instance, the counter may be obtained based on the number of times the network device is woken up, and may be updated whenever the network device is woken up. When the counter is updated, an input value may be generated using a WAC that was used in a previous wake-up operation, instead of using the initial vector, so that the WAC may be updated.

EFFECT

According to example embodiments, a network device may wake up a main circuit unit using an energy obtained from a wake-up radio signal, which is received using a Radio-Frequency Identification (RFID) receiver in an Industrial, Scientific and Medical (ISM) band, may authenticate the wake-up radio signal based on a Wake-up Authentication Code (WAC) contained in the wake-up radio signal, and may communicate with a network control device in a Medical Implant Communication Service (MICS) frequency band. Here, the network device may wake up the main circuit unit using the energy contained in the wake-up radio signal, rather than using a separate battery, and thus it is possible to reduce energy consumption.

Also, according to example embodiments, a network control device may transmit a wake-up radio signal to a network device using an RFID receiver, may receive a response signal from the network device which is woken up in response to the wake-up radio signal, and may communicate with the network device. In this instance, the ISM band may be used instead of the MICS band to transmit the wake-up radio signal to the network device, and thus it is possible to reduce a transmission power level.

Also, according to example embodiments, a network device may generate a WAC using at least one of a counter obtained based on the number of times the network device is woken up, an address for the network device, an address for a network control device, and a key shared between the network device and the network control device. Therefore, it is possible to prevent other users without the shared key from waking up the network device.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

To increase the lifespan of devices in a Wireless Body Area Network (WBAN), each of specially implanted sensor devices must maximize energy conservation. A wake-up and sleep scheme using a wake-up radio signal is considered a viable approach. A variety of wake-up schemes have been proposed for a Wireless Sensor Network (WSN). However, the security of wake-up radio signals is still an open issue. Security in a wake-up scheme is among the top criteria in WBAN when considering adoption of the wake-up scheme.

In example embodiments, a network device and a network control device in a WBAN, and a secure wake-up method for WBANs are provided. In the secure wake-up method, a Wake-up Authentication Code (WAC) is proposed to guarantee that a BAN Node (BN) is woken up by a corresponding BAN Network Controller (BNC), rather than unintentionally or maliciously by external users. Also, a two-radio architecture may be proposed. The proposed secure wake-up method provides a suitable tradeoff between security and energy consumption.

As described above, example embodiments relate to the secure wake-up method for WBANs. In the secure wake-up scheme for WBANs, a WAC may be preferentially designed to guarantee that a BN is woken up by a corresponding BNC rather than unintentionally or maliciously by external users. Instead of addresses of BNs, a WAC is the unique code associating each BN with a corresponding BNC. To design the WAC, a secure key generation scheme may be used. To prevent other users without a secret key from waking up a BN, the WAC may provide authentication and freshness for each wake-up process, which is derived from the generation algorithm-Advanced Encryption Standard (AES) where a counter and addresses for a BNC and a BN are used as input values.

Figure 1:
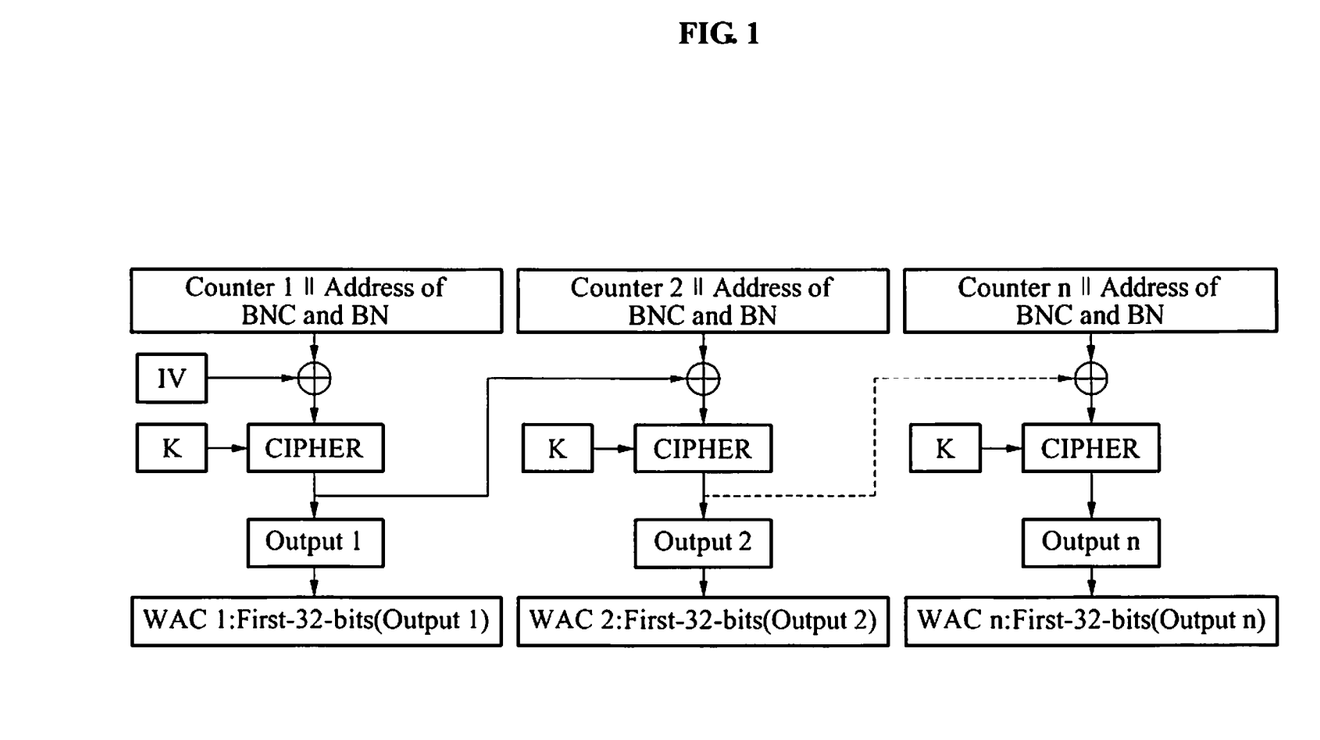
FIG. 1 is a diagram illustrating a method of generating a Wake-up Authentication Code (WAC) according to example embodiments.

FIG. 1 is a diagram illustrating a method of generating a WAC according to example embodiments. In FIG. 1, symbol "||" denotes a connection of left and right operands, "CIPHER" denotes an AES algorithm, "IV" denotes an initial vector, and "K" denotes a secret key. For example, the length of the counter may be set to two octets, to make a counter space large enough to ensure the uniqueness of the WAC and to avoid compromised security where the same secret key is provided in the operation of the counter. The counter may have a value obtained based on the number of times the BN is woken up. In FIG. 1, the counter is incremented by "1" whenever the BN is woken up. In this instance, when an initial WAC is generated, Counter "1" and the addresses of the BNC and BN are connected so as to be used as an initial input value. A bitwise Exclusive OR (XOR) operation may be performed with the initial input value and the initial vector, so that an input value of the AES algorithm may be generated. An initial WAC may be generated based on the generated input value, the secret key and "Output 1," namely, an output value generated through the AES algorithm. Subsequently, when the counter is incremented, that is, when the BN is woken up, the WAC may be used instead of the initial vector. In other words, the WAC may be XOR-ed with the initial input unit, and a value obtained by the XOR operation may be generated as an input value of the AES algorithm. In this instance, "Output 2," namely, an output value of the AES algorithm using the input value and the secret key may be generated as a new WAC. Also, the WAC may be updated whenever the BN is woken up. This operation may be performed in both the BN and the BNC.

Figure 2:
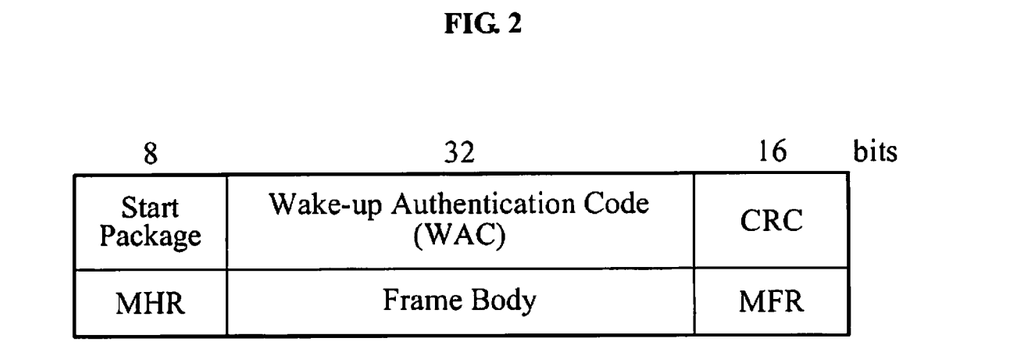
FIG. 2 is a diagram illustrating a format of a wake-up packet according to example embodiments.

FIG. 2 is a diagram illustrating a format of a wake-up packet according to example embodiments. A data field of the wake-up packet transmitted through a wake-up radio signal may include a WAC field having a size of 32 bits. The WAC may be contained in a "WAC" field in the BNC, and a wake-up packet containing the WAC may be transmitted to the BN through the wake-up radio signal.

Figure 3:
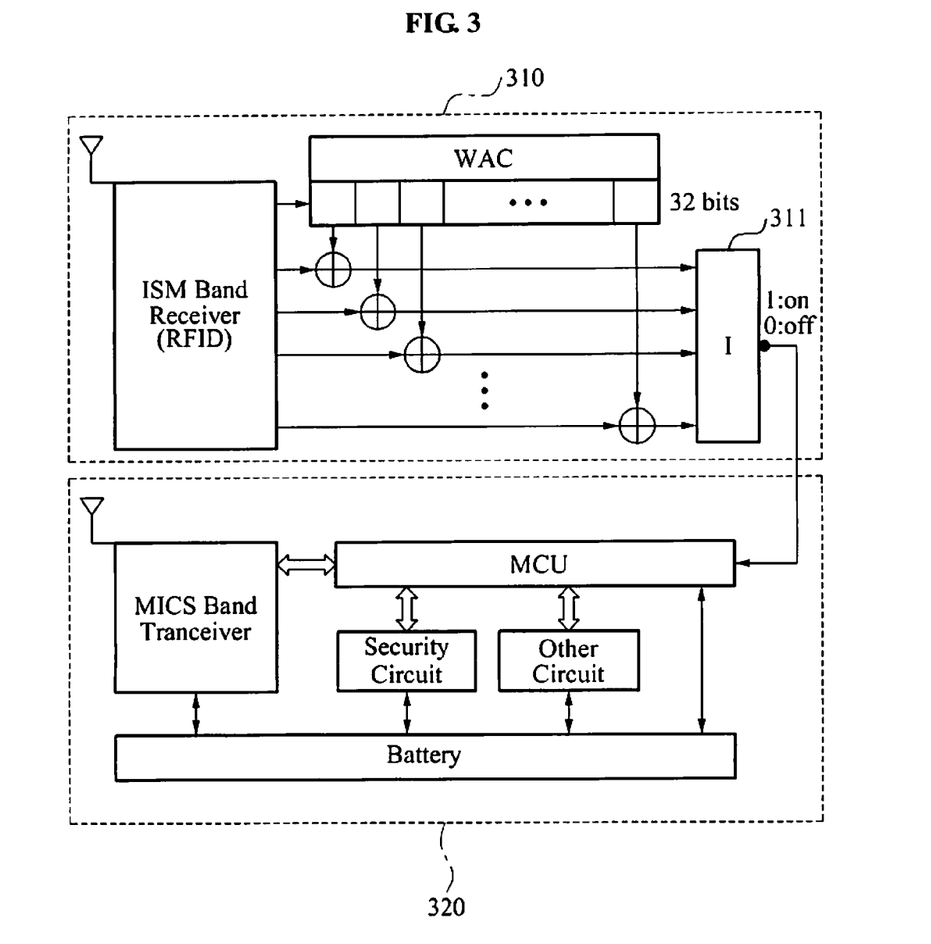
FIG. 3 is a diagram illustrating a two-radio architecture according to example embodiments.

FIG. 3 is a diagram illustrating a two-radio architecture according to example embodiments. Since a wake-up radio signal containing a WAC may not be transmitted in a Medical Implant Communication Service (MICS) frequency band due to Federal Communications Commission (FCC) rules, a two-radio architecture for a MICS band and an Industrial, Scientific and Medical (ISM) band may be used in the BN. The BN may include, for example, a passive Radio-Frequency IDentification (RFID) circuit as a special hardware component. Also, the BN may receive the wake-up radio signal, and may be driven using an energy contained in the received wake-up radio signal. The BN may verify whether the WAC contained in the wake-up radio signal is identical to a WAC stored in memory. When the WAC contained in the wake-up radio signal is identical to a WAC stored in memory, the BN may wake up a main circuit unit. As a result of the introduction of RFID technology, a wake-up system according to example embodiments is not necessary to supply an energy to a wake-up circuit.

Referring to FIG. 3, a first dotted-line box 310 shows a situation where a wake-up radio signal is received using an RFID receiver as an ISM band receiver, whether a WAC contained in the received wake-up radio signal is identical to a WAC stored in advance is determined after comparing the two WACs, and an interrupt signal is transmitted to a microcontroller unit (MCU) when the two WACs are determined to be identical to each other. Specifically, to compare the two WACs, a bitwise XOR operation may be performed on the two WACs, and NOT operations may be performed by an inverse unit "I" 311 for each result of the bitwise XOR operation. When bits obtained by the NOT operations are all "1," the main circuit unit may be turned "on," to enter a wake-up mode. Alternatively, when at least one of the bits is not "1," the main circuit unit may be turned "off," to enter sleep mode. Herein, an example of using the bitwise XOR operation has been described above, but is not limited thereto. Accordingly, a variety of methods of checking whether the two WACs are identical to each other may be used instead of the bitwise XOR operation.

In FIG. 3, a second dotted-line box 320 shows the main circuit unit. A "MICS Band Transceiver" indicates a MICS transceiver enabling communication with a BNC in the MICS band, and a "Security Circuit" indicates a security circuit enabling updating of a counter and a WAC.

This design provides a solid foundation for hardware implementation of the following method.

Figure 4:
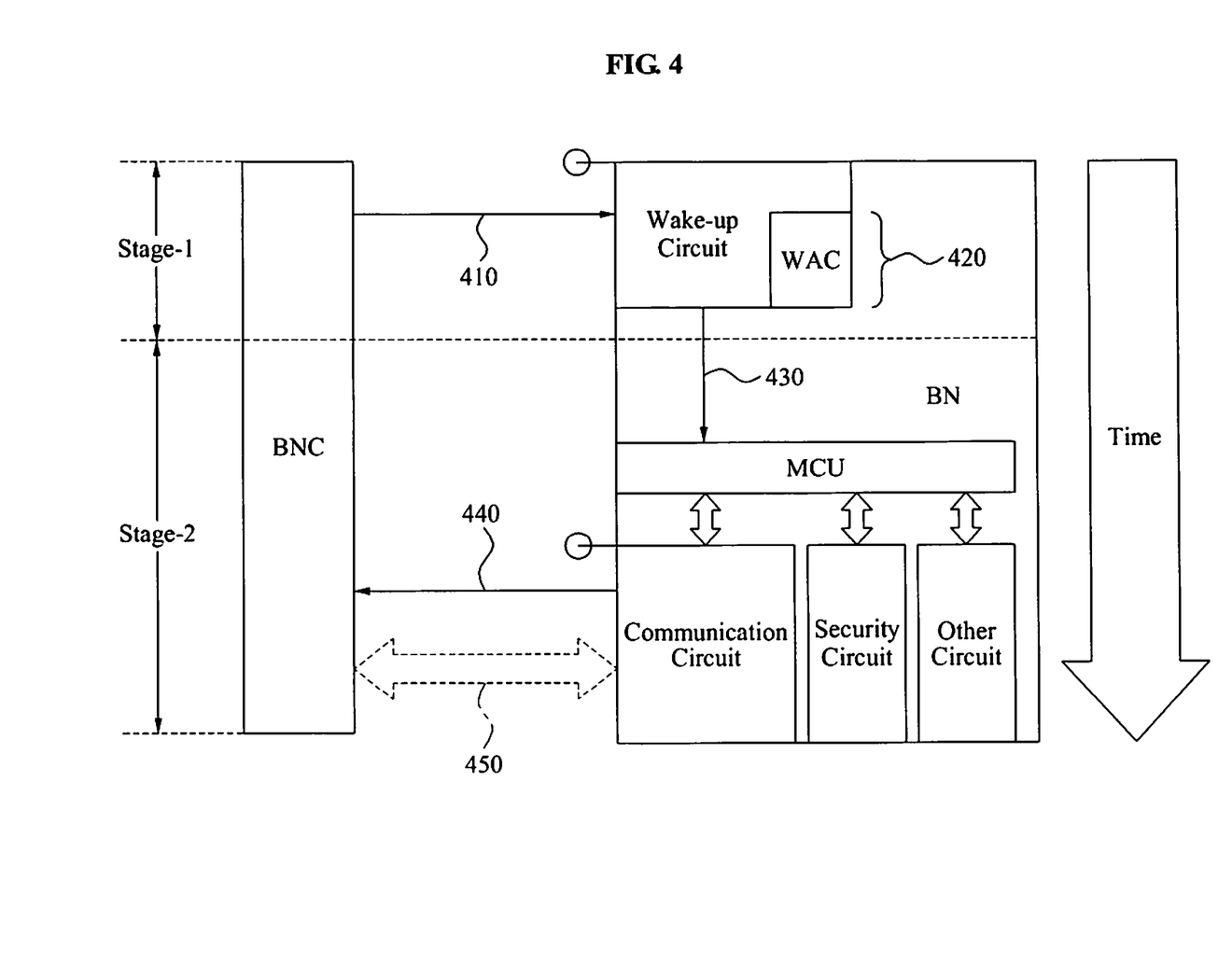
FIG. 4 is a diagram illustrating a secure wake-up method performed between a Body Area Network Controller (BNC) and a Body Area Network node (BN) according to example embodiments.

FIG. 4 is a diagram illustrating a secure wake-up method between a BNC and a BN according to example embodiments. The secure wake-up method of FIG. 4 may include two stages based on the two-radio architecture described above with reference to FIG. 3. Referring to FIG. 4, in Stage-1, while the main circuit unit is in the sleep mode, a wake-up circuit may be driven only by an energy contained in a wake-up radio signal. In Stage-2 after passing Stage-1, the main circuit unit may be activated by the wake-up circuit, and an operation state of the main circuit unit may be changed.

In operation 410, the BNC may transmit the wake-up radio signal containing a WAC to the BN in the sleep mode in the ISM band. In this instance, the RFID technology may be employed to transmit the wake-up radio signal. The wake-up circuit of the BN may be driven using the energy contained in the received wake-up radio signal. For example, the wake-up circuit of the BN may perform operations 420 and 430 using the energy contained in the wake-up radio signal.

In operation 402, after receiving the wake-up radio signal, the BN may accumulation the energy contained in the wake-up radio signal, and may compare the WAC contained in the received wake-up radio signal with a WAC stored in advance. When the two WACs are determined to be identical to each other as a result of the comparing, the wake-up circuit of the BN may perform operation 403. Alternatively, when the two WACs are determined to be different from each other, the wake-up circuit of the BN may no longer stop being driven.

In operation 403, the wake-up circuit of the BN may transmit an interrupt signal to the MCU of the BN, to activate the main circuit unit using the accumulated energy contained in the wake-up radio signal received by the RFID receiver.

In operation 440, a communication circuit in the main circuit unit of the BN may transmit a response signal to the BNC.

In operation 450, both the BNC and the BN may update the counter by incrementing the counter, and may update the WAC by calculating an output of the AES algorithm based on inputs of the updated counter, a shared key, and addresses of the BNC and the BN. For example, the counter and the WAC may be updated by a security circuit in the BN. The BNC and the BN may maintain synchronization of the counter by updating the counter. After updating the counter, the BNC and BN may enter a normal communication mode.

In the secure wake-up method illustrated in FIG. 4, the wake-up circuit may be used as a receiver, rather than a transmitter. Using the wake-up circuit as a receiver may reduce the complexity of the wake-up circuit, lower a transmission power of the wake-up radio signal transmitted from the BNC to the BN in the ISM band, and decrease a need for the energy contained in the wake-up radio signal. The wake-up circuit of the BN may not transmit any data, such as a response signal, in Stage-1. Both control data and sensor data may be transmitted to the BNC by the communication circuit in the main circuit, after a successful authentication of the WAC. Therefore, the use of the WAC may completely and easily prevent the BN from being inadvertently or maliciously woken up by external devices.

Figure 5:
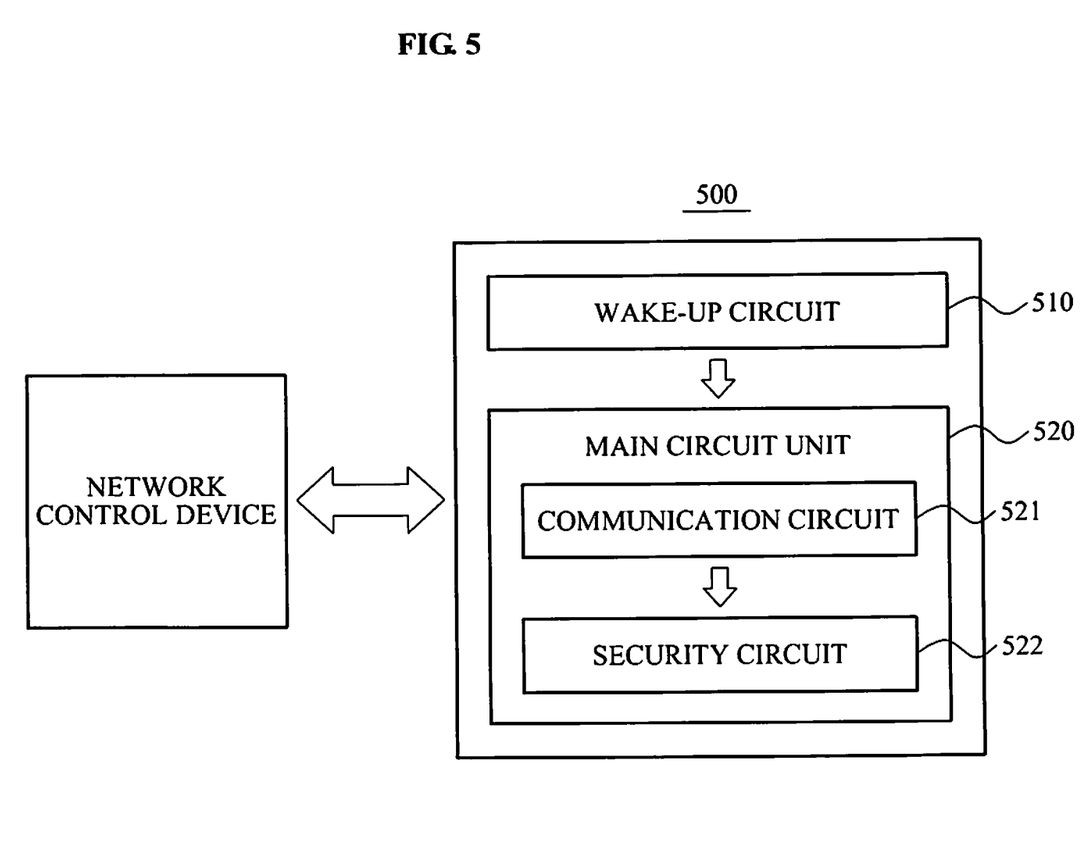
FIG. 5 is a block diagram illustrating a configuration of a network device according to example embodiments.

FIG. 5 is a block diagram illustrating a configuration of a network device 500 according to example embodiments. The network device 500 of FIG. 5 may correspond to the BN described above with reference to FIGS. 1 to 4. As shown in FIG. 5, the network device 500 may include a wake-up circuit 510 and a main circuit unit 520.

The wake-up circuit 510 may receive a wake-up radio signal from a network control device using an RFID receiver, may compare a WAC contained in the received wake-up radio signal with a WAC stored in advance, and may determine whether to wake up the main circuit unit 520. Here, the network control device may be contained in the WBAN.

The main circuit unit 520 may be woken up in response to an interrupt signal from the wake-up circuit 510. In this instance, the interrupt signal may be generated by the wake-up circuit 510 using an energy contained in the wake-up radio signal. After the main circuit unit 520 is woken up, the main circuit unit 520 may transmit a response signal to the network control device, and may update a counter and the WAC. To perform the transmitting and updating, the main circuit unit 520 may include a communication circuit 521 and a security circuit 522, as shown in FIG. 5. In this instance, the main circuit unit 520 may further include an MCU for receiving an interrupt signal and converting a current mode of the main circuit unit 520 to the wake-up mode as illustrated in FIGS. 4 and 5.

The communication circuit 521 may transmit a response signal to the network control device, after the main circuit unit 520 is woken up in response to the interrupt signal. The MICS band may be used to transmit the response signal to the network control device.

The security circuit 522 may update the counter, and update the stored WAC based on at least one of the updated counter, an address for the security circuit, an address for the network control device, and a key shared with the network control device. The shared key may correspond to the secret key described above with reference to FIGS. 1 to 4.

After the security circuit 522 updates the WAC, the communication circuit 521 may transmit sensed data or monitored data to the network control device. In other words, the communication circuit 521 may enter the normal communication mode with the network control device. Here, the MICS band may be used to transceive data between the communication circuit 521 and the network control device.

Figure 6:
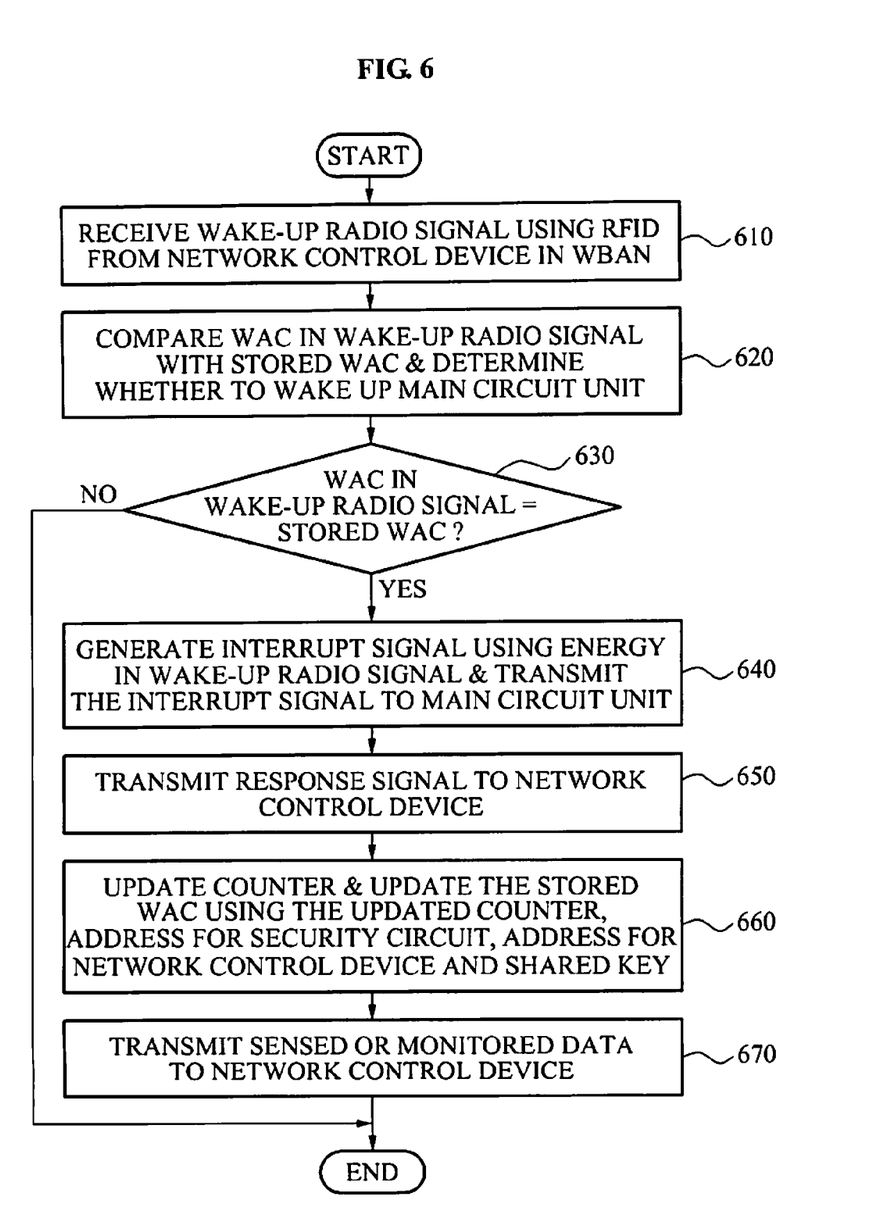
FIG. 6 is a flowchart illustrating a secure wake-up method in a network device according to example embodiments.

FIG. 6 is a flowchart illustrating a secure wake-up method in a network device according to example embodiments. The secure wake-up method of FIG. 6 may be performed by the network device contained in the WBAN. Hereinafter, each operation of the secure wake-up method of FIG. 6 will be described.

In operation 610, a wake-up circuit of the network device receives a wake-up radio signal using an RFID receiver from a network control device contained in the WBAN.

In operation 620, the wake-up circuit compares a WAC contained in the received wake-up radio signal with a WAC stored in advance, and determines whether to wake up a main circuit unit of the network device.

When the WAC in the wake-up radio signal is determined to be identical to the stored WAC in operation 630, the wake-up circuit performs operation 640. Alternatively, when the two WACs are determined to be different from each other, the wake-up circuit aborts the secure wake-up method.

In operation 640, the wake-up circuit generates an interrupt signal using an energy contained in the wake-up radio signal, and transmits the generated interrupt signal to the main circuit unit of the network device.

In operation 650, a communication circuit in the main circuit unit transmits a response signal to the network control device, after the main circuit unit is woken up in response to the interrupt signal.

In operation 660, a security circuit in the main circuit unit updates a counter, and updates the stored WAC based on at least one of the updated counter, an address for the security circuit, an address for the network control device, and a key shared with the network control device. Here, the shared key may correspond to the secret key described above with reference to FIGS. 1 to 4.

In operation 670, the communication circuit transmits sensed or monitored data to the network control device. In other words, the communication circuit enters the normal communication mode with the network control device. Here, the MICS band may be used to transceive data between the communication circuit and the network control device.

Operations of FIGS. 5 and 6 may be further understood with reference to FIGS. 1 to 4 and the corresponding descriptions thereof, and accordingly, additional descriptions will be omitted herein. For example, operations 610 to 640 may correspond to Stage-1 described with reference to FIG. 4, and operations 650 to 670 may correspond to Stage-2 described with reference to FIG. 4.

As described above, in the secure wake-up method according to example embodiments, the network device may wake up the main circuit unit using the energy obtained from the wake-up radio signal, which is received by the network device using the RFID receiver in the ISM band, may authenticate the wake-up radio signal based on the WAC contained in the wake-up radio signal, and may communicate with the network control device in the MICS band. Here, the network device may wake up the main circuit unit using the energy contained in the wake-up radio signal, rather than using a separate battery and thus, may reduce energy consumption.

Figure 7:
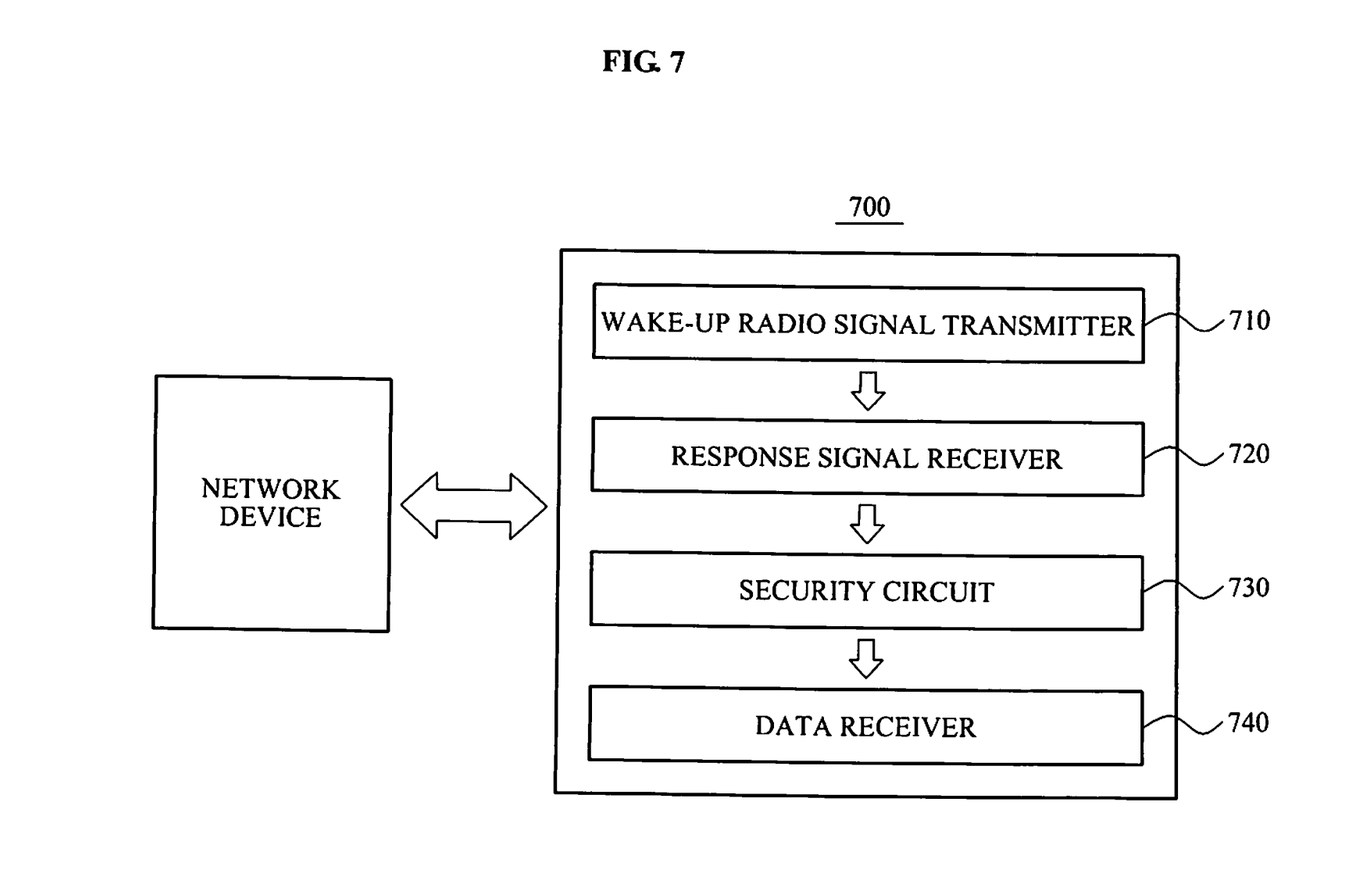
FIG. 7 is a block diagram illustrating a configuration of a network control device according to example embodiments.

FIG. 7 is a block diagram illustrating a configuration of a network control device 700 according to example embodiments. The network control device 700 of FIG. 7 may correspond to the BNC described above with reference to FIGS. 1 to 4. As shown in FIG. 7, the network control device 700 may include a wake-up radio signal transmitter 710, a response signal receiver 720, a security circuit 730 and a data receiver 740.

The wake-up radio signal transmitter 710 may transmit a wake-up radio signal containing a WAC to a network device using an RFID receiver. Here, the network device may be contained in a WBAN. In this instance, the ISM band may be used by the network control device 700 to transmit the wake-up radio signal at a relatively low transmission power level compared with the MICS band and thus, may reduce battery consumption.

The response signal receiver 720 may receive a response signal from the network device, when a main circuit unit of the network device is woken up based on the WAC. In this instance, to wake up the main circuit unit of the network device, an interrupt signal may be generated using an energy contained in the wake-up radio signal. When the WAC in the wake-up radio signal is identical to a WAC stored in the network device, the interrupt signal may be generated. In other words, the network device may be woken up only when the wake-up radio signal is authenticated based on the WAC and thus, may prevent other users without a secret key from waking up the network device.

After the response signal is received, the security circuit 730 may update a counter, and may update the WAC based on at least one of the updated counter, an address for the security circuit, an address for the network device, and a key shared with the network device. Here, the shared key may correspond to the secret key described above.

The data receiver 740 may receive the data sensed or monitored by the network device from the network device. In other words, the data receiver 740 may enter the normal communication mode with the network device. Here, the MICS band may be used to transceive data between the data receiver 740 and the network device.

Figure 8:
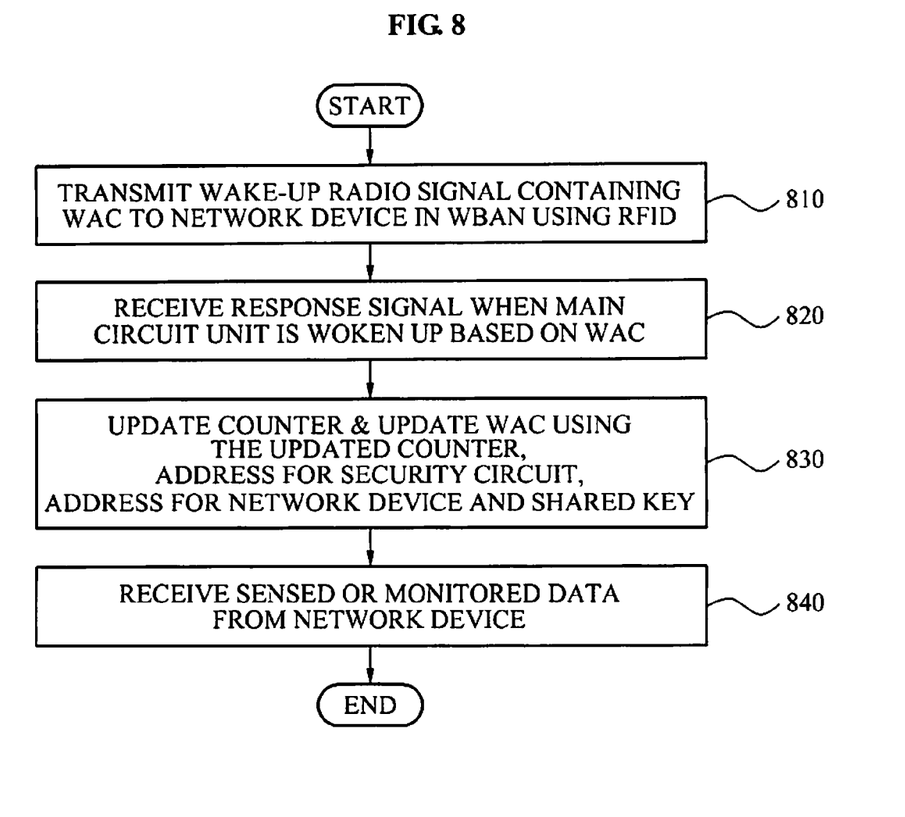
FIG. 8 is a flowchart illustrating a secure wake-up method in a network control device according to example embodiments.

FIG. 8 is a flowchart illustrating a secure wake-up method in a network control device according to example embodiments. The secure wake-up method of FIG. 8 may be performed by the network control device contained in the WBAN. Hereinafter, each operation of the secure wake-up method of FIG. 8 will be described.

In operation 810, a wake-up radio signal transmitter of the network control device transmits a wake-up radio signal containing a WAC to a network device using an RFID receiver. Here, the network device may be contained in the WBAN. In this instance, the ISM band may be used to transmit the wake-up radio signal at a relatively low transmission power level compared with the MICS band and thus, may reduce battery consumption.

In operation 820, a response signal receiver of the network control device receives a response signal from the network device, when a main circuit unit of the network device is woken up based on the WAC. In this instance, to wake up the main circuit unit of the network device, an interrupt signal may be generated using an energy contained in the wake-up radio signal. When the WAC in the wake-up radio signal is identical to a WAC stored in the network device, the interrupt signal may be generated. In other words, the network device may be woken up only when the wake-up radio signal is authenticated based on the WAC and thus, may prevent other users without a secret key from waking up the network device.

In operation 830, a security circuit of the network control device updates a counter, and updates the WAC based on at least one of the updated counter, an address for the security circuit, an address for the network device, and a key shared with the network device. Here, the shared key may correspond to the secret key described above.

In operation 840, a data receiver of the network control device receives the data sensed or monitored by the network device from the network device. In other words, the data receiver may enter the normal communication mode with the network device. Here, the MICS band may be used to transceive data between the data receiver and the network device.

Operations of FIGS. 7 and 8 may be further understood with reference to FIGS. 1 to 4 and the corresponding descriptions thereof, and accordingly, additional descriptions will be omitted herein.

As described above, in the secure wake-up method according to example embodiments, the network control device may transmit the wake-up radio signal to the network device using the RFID receiver, may receive the response signal from the network device woken up in response to the wake-up radio signal, and may communicate with the network device. In this instance, the ISM band may be used instead of the MICS band to transmit the wake-up radio signal to the network device and thus, may reduce a transmission power level.

Figure 9:
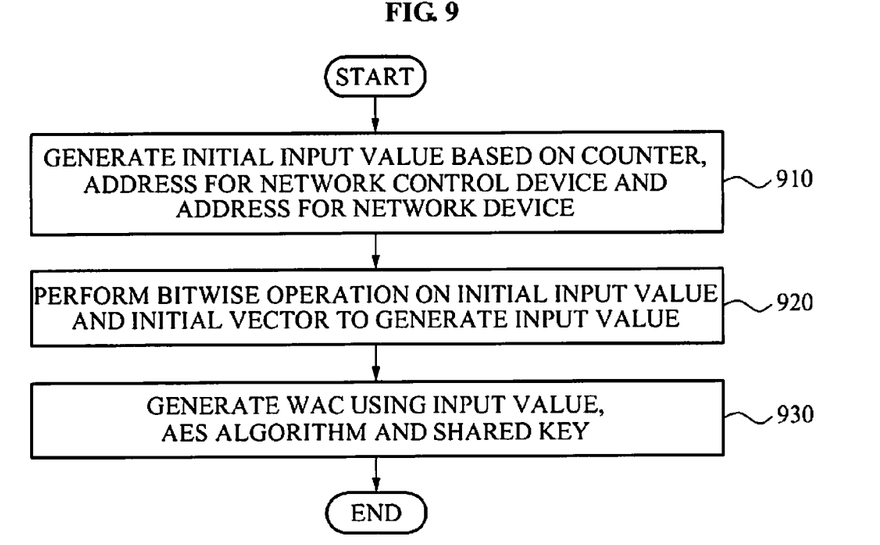
FIG. 9 is a flowchart illustrating a method of generating a WAC in a network control device or in a network device according to example embodiments.

FIG. 9 is a flowchart illustrating a method of generating a WAC in a network control device or in a network device, according to example embodiments.

In operation 910, the network control device or the network device generates an initial input value based on at least one of a counter, an address for the network control device and an address for the network device. Here, the counter may be obtained based on the number of times the network device is woken up, and may be updated whenever the network device is woken up.

In operation 920, the network control device or the network device performs a bitwise operation on the initial input value and an initial vector, to generate an input value. Specifically, when the counter is updated, the network control device or the network device may generate an input value using a WAC that was used in a previous wake-up operation, instead of using the initial vector, so that the WAC may be updated.

In operation 930, the network control device or the network device generates a WAC using the input value, the AES algorithm and a key shared between the network control device and the network device.

In other words, after an initial WAC is generated, the initial WAC may be updated using a WAC that was used in a previous wake-up operation, instead of using the initial vector.

Operations of FIG. 9 may be further understood with reference to FIGS. 1 to 4 and the corresponding descriptions thereof, and accordingly, additional descriptions will be omitted herein.

As described above, in the method of generating a WAC according to example embodiments, a WAC may be generated using at least one of the counter obtained based on the number of times the network device is woken up, the address for the network control device, the address for the network device and the key shared between the network control device and the network device. Thus, other users without the shared key may be prevented from waking up the network device.

The above-described example embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A network device contained in a Wireless Body Area Network (WBAN), the network device comprising:
   a wake-up circuit to receive a wake-up radio signal from a network control device using a Radio-Frequency Identification (RFID) receiver, to compare a Wake-up Authentication Code (WAC) contained in the received wake-up radio signal with a WAC stored in advance, and to determine whether to wake up a main circuit unit, the network control device being contained in the WBAN; and
   the main circuit unit to be woken up in response to an interrupt signal from the wake-up circuit;
   wherein the main circuit unit comprises:
   a communication circuit to transmit a response signal to the network control device, after the main circuit unit is woken up in response to the interrupt signal; and
   a security circuit to update a counter, and to update the stored WAC based on at least one of the updated counter, an address for the security circuit, an address for the network control device, and a key shared with the network control device, in response to the interrupt signal from the wake-up circuit.

2. The network device of claim 1, wherein, after the security circuit updates the WAC, the communication circuit transmits data to the network control device, the data being sensed or monitored.

3. A network control device contained in a WBAN, the network control device comprising:
   a wake-up radio signal transmitter to transmit a wake-up radio signal containing a WAC to a network device using an RFID receiver, the network device being contained in the WBAN; and
   a response signal receiver to receive a response signal from the network device when a main circuit unit of the network device is woken up based on the WAC,
   a security circuit to update a counter, and to update the WAC based on at least one of the updated counter, an address for the security circuit, an address for the network device, and a key shared with the network device, in response to an interrupt signal; and
   wherein the interrupt signal is generated using an energy contained in the wake-up radio signal, to wake up the main circuit unit.

4. A secure wake-up method in a network device contained in a WBAN, the secure wake-up method comprising:
   receiving, by a wake-up circuit of the network device, a wake-up radio signal from a network control device using an RFID receiver, the network control device being contained in the WBAN;
   comparing, by the wake-up circuit, a WAC contained in the received wake-up radio signal with a WAC stored in advance, and determining whether to wake up a main circuit unit of the network device;
   generating, by the wake-up circuit, an interrupt signal using an energy contained in the wake-up radio signal, and transmitting the generated interrupt signal to the main circuit unit;
   transmitting, by a communication circuit of the main circuit unit, a response signal to the network control device, the main circuit unit being woken up in response to the interrupt signal;
   updating, by a security circuit of the main circuit unit, a counter, and updating the stored WAC based on at least one of the updated counter, an address for the security circuit, an address for the network control device, and a key shared with the network control device, in response to the interrupt signal from the wake-up circuit; and
   transmitting, by the communication circuit, data to the network control device, the data being sensed or monitored.

\* \* \* \* \*